(12) United States Patent
Cheng et al.

(10) Patent No.: US 10,188,700 B2
(45) Date of Patent: *Jan. 29, 2019

(54) USE OF HAPTOGLOBIN SUBUNIT FOR PROMOTING ANGIOGENESIS

(71) Applicant: Taipei Medical University, Taipei (TW)

(72) Inventors: Tsai-Mu Cheng, Taipei (TW); Che-Chang Chang, Taipei (TW)

(73) Assignee: TAIPEI MEDICAL UNIVERSITY, Taipei (TW)

( * ) Notice: Subject to any disclaimer, the term of this patent is extended or adjusted under 35 U.S.C. 154(b) by 63 days.

This patent is subject to a terminal disclaimer.

(21) Appl. No.: 15/371,231

(22) Filed: Dec. 7, 2016

(65) Prior Publication Data

US 2018/0036370 A1 Feb. 8, 2018

(30) Foreign Application Priority Data

Aug. 4, 2016 (TW) .............................. 105124776 A

(51) Int. Cl.
*A61K 38/00* (2006.01)
*A61K 38/17* (2006.01)

(52) U.S. Cl.
CPC ................................. *A61K 38/1709* (2013.01)

(58) Field of Classification Search
None
See application file for complete search history.

(56) References Cited

U.S. PATENT DOCUMENTS 5,318,957 A * 6/1994 Cid .................... C07K 14/4717
514/13.3
9,260,497 B2 * 2/2016 Kim .................... C07K 14/4717

FOREIGN PATENT DOCUMENTS

WO     WO 2014/112702 A1 *  7/2014

* cited by examiner

*Primary Examiner* — Christina Bradley
(74) *Attorney, Agent, or Firm* — Locke Lord LLP; Tim Tingkang Xia, Esq.

(57) ABSTRACT

Provided is a method for promotion of angiogenesis, comprising: administering a haptoglobin subunit to a subject in need thereof. Also provided is a method for treating a disease related to defective angiogenesis, comprising: administering a haptoglobin subunit to a subject in need thereof. Further provided is a method for promotion of angiogenesis, comprising: administering a modified haptoglobin subunit to a subject in need thereof, the modified haptoglobin subunit comprising an amino acid sequence selected from one of SEQ ID NOs: 1-3. Additionally provided is a method for treating a disease related to defective angiogenesis, comprising: administering a modified haptoglobin subunit to a subject in need thereof, the modified haptoglobin subunit comprising an amino acid sequence selected from one of SEQ ID NOs: 1-3.

7 Claims, 5 Drawing Sheets

Specification includes a Sequence Listing.

USE OF HAPTOGLOBIN SUBUNIT FOR PROMOTING ANGIOGENESIS

CROSS REFERENCE

The non-provisional application claims priority from Taiwan Patent Application NO. 105124776, filed on Aug. 4, 2016, the content thereof is incorporated by reference herein.

FIELD OF THE INVENTION

The present invention relates to pharmaceutical use of a haptoglobin (Hp) subunit, and in particular to, use of a haptoglobin subunit for angiogenesis promotion.

BACKGROUND OF THE INVENTION

Angiogenesis is a physiological phenomenon, in which a blood supply system is developed by formation of new vascular networks from pre-existing blood vessels. In angiogenesis, extravascular cells secret various signal factors to activate and mediate migration, growth, and proliferation of intravascular cells. These signal factors are called "angiogenic factors", which not only promote the angiogenesis but also trigger repair of damaged blood vessels.

When requirement of blood vessels in tissues is due to hypoxia, secretion level of angiogenic factors increases so as to enhance opportunity of angiogenesis. Therefore, if a novel drug for angiogenesis promotion is developed, it can promote the blood stream of an affected region in a patient suffered from a certain disease, such as a cardiovascular disease, a myocardial infraction, or an ischemic disease. In such a manner, the affected region gains nutrients to recover the tissues and normalizes the ability to deliver blood and oxygen.

SUMMARY OF THE INVENTION

A first aspect of the present invention is to provide a method for promotion of angiogenesis, and the provided method comprises: administering a haptoglobin subunit to a subject in need thereof. In some embodiments, the haptoglobin subunit is present in form of a haptoglobin 1-1 protein, a haptoglobin 2-1 protein, or a haptoglobin 2-2 protein.

In other embodiments, the haptoglobin subunit is selected from a haptoglobin α1 subunit, a haptoglobin α2 subunit, or a haptoglobin β subunit.

In further embodiments, each haptoglobin protein is obtained via purification from blood, gene engineering, or chemical synthesis.

In still other embodiments, the haptoglobin subunit is obtained via purification from blood, gene engineering, or chemical synthesis.

In yet other embodiments, the haptoglobin subunit inhibits inflammatory response and/or promotes cell proliferation.

A second aspect of the present invention is to provide a method for treating a disease related to defective angiogenesis, and the provided method comprises: administering a haptoglobin subunit to a subject in need thereof.

In some embodiments, the haptoglobin subunit is present in form of a haptoglobin 1-1 protein, a haptoglobin 2-1 protein, or a haptoglobin 2-2 protein.

In other embodiments, the haptoglobin subunit is selected from a haptoglobin α1 subunit, a haptoglobin α2 subunit, or a haptoglobin β subunit.

In further embodiments, each haptoglobin protein is obtained via purification from blood, gene engineering, or chemical synthesis.

In still other embodiments, the haptoglobin subunit is obtained via purification from blood, gene engineering, or chemical synthesis.

In yet other embodiments, the disease is selected from a cardiovascular disease, a myocardial infraction, or an ischemic disease.

In yet other embodiments, the haptoglobin subunit inhibits inflammatory response and/or promotes cell proliferation.

A third aspect of the present invention is to provide a method for promotion of angiogenesis, and the provided method comprises: administering a modified haptoglobin subunit to a subject in need thereof, the modified haptoglobin subunit comprising an amino acid sequence selected from one of SEQ ID NOs: 1-3.

In some embodiments, the modified haptoglobin subunit is obtained via gene engineering or chemical synthesis.

In other embodiments, the modified haptoglobin subunit inhibits inflammatory response and/or promotes cell proliferation.

The foregoing sequences of SEQ ID NOs: 1-3 are designed according to substitution of alanine (Ala) residues for some cysteine (Cys) residues in a native haptoglobin α1 subunit, α2 subunit, and β subunit, respectively. Therefore, disulfide bond formation in the modified haptoglobin subunit can reduce so as to facilitate protein purification.

A fourth aspect of the present invention is to provide a method for treating a disease related to defective angiogenesis, and the provided method comprises: administering a modified haptoglobin subunit to a subject in need thereof, the modified haptoglobin subunit comprising an amino acid sequence selected from one of SEQ ID NOs: 1-3.

In some embodiments, the modified haptoglobin subunit is obtained via gene engineering or chemical synthesis.

In other embodiments, the disease is selected from a cardiovascular disease, a myocardial infraction, or an ischemic disease.

In further embodiments, the modified haptoglobin subunit inhibits inflammatory response and/or promotes cell proliferation.

The foregoing sequences of SEQ ID NOs: 1-3 are designed through substitution of Ala residues for some Cys residues in a native haptoglobin α1 subunit, α2 subunit, and β subunit, respectively. Accordingly, disulfide bond formation in the modified haptoglobin subunit can reduce so as to facilitate protein purification.

DETAILED DESCRIPTION OF THE INVENTION

The detailed description and preferred embodiment of the invention will be set forth in the following content, and provided for people skilled in the art so as to understand the characteristic of the invention.

EXAMPLE 1

Cell Culture

Human umbilical vein endothelial cells (HUVECs) were purchased from the Bioresource Collection and Research Center (BCRC). All cells were cultured in M199 medium supplemented with 15% heat-inactivated fetal bovine serum (FBS), 100 U/mL of penicillin, 100 μg/mL of streptomycin, 25 μg/mL of gentamycin, 5 μg/mL of Ara-C, and 25 μg/mL of endothelial cell growth supplement (Sigma). These cells were placed in a 10cm culture dish, and maintained under an environment of 37° C. and 5% $CO_2$ for 5-6 days. These cells were used in future experiments when growing to 90% confluence.

EXAMPLE 2

Anti-Inflammation Test

Monocyte chemoattractant protein-1 (MCP-1) expression level in patients suffered from an acute myocardial infarction is elevated, which indicates that MCP-1 is related to plaque rupture and remodeling of vascular walls. Furthermore, an in-situ hybridization method or an immunostaining method can be introduced to identify MCP-1 mRNA expression level and its protein expression level in cardiac muscles from patients or animals.

Human and animal experiment has proven that MCP-1 is related to neointimal hyperplasia-related restenosis after percutaneous coronary intervention. Other research has demonstrated that MCP-1 is related to inflammatory response. Other research has demonstrated that elevation of MCP-1 expression level leads to death of cardiomyoblast cells, and MCP-1 also binds to MCP-1-induced protein so as to give rise to heart failure. Therefore, any method for suppressing MCP-1 expression may be tried to remit inflammatory response in a cardiovascular system.

Figure 1:
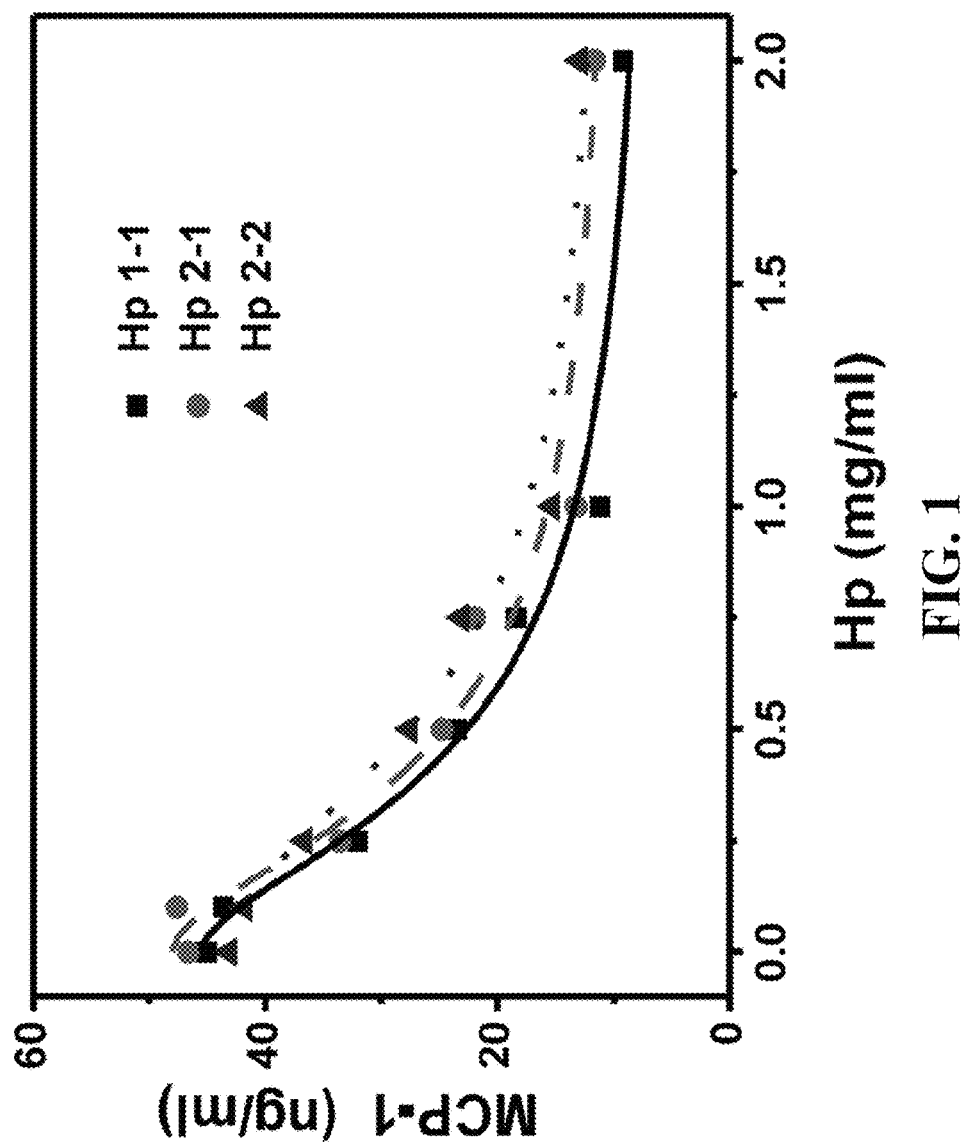
FIG. 1 is a curve graph illustrating MCP-1 protein expression level in HUVECs treated with each Hp phenotype in different concentrations.

In order to determine whether an Hp protein has effect on inflammatory response in HUVECs induced by a protein kinase c (PKC) activator, phorbol myristate acetate (PMA), Hp proteins were added to HUVECs having inflammatory response induced by PMA, and then MCP-1 expression level in these cells was measured. At the same time, anti-inflammation caused by various Hp phenotypes was compared. Specifically, HUVECs were incubated with various Hp phenotypes in different concentrations for 8 hours, and then incubated with 100 ng/mL of PMA for other 8 hours. As shown in FIG. 1, an Hp protein can inhibit MCP-1 secretion level induced by PMA in a dose-dependent manner. Since HUVECs cannot secret MCP-1 by themselves, the foregoing result demonstrates an Hp protein can ease PMA-induced inflammatory response. In another aspect, inhibition of MCP-1 expression by an Hp 1-1 protein in an effective concentration, 2 mg/mL, prevails against that by the other Hp phenotypes (90% inhibition level for an Hp 1-1 protein; 79% inhibition level for an Hp 2-1 protein; 66% inhibition level for an Hp 2-2 protein). As such, an Hp protein can suppress secretion (expression) level of PMA-induced MCP-1 in HUVECs. That is, an Hp protein has the anti-inflammation potential.

In transgenic mice overexpressing MCP-1, MCP-1 can recruit monocytes to an atheroma, and induce formation of foam cells and atherosclerosis. The phenomena include chemotaxis to MCP-1 requiring human monocytes' protein kinase c (PKC). A PKC agonist, PMA, can induce shedding of CD163 through activation of PKC. Current research has shown that soluble CD163 secretion mechanism by human monocytes is significant for regulation of inflammatory response. According to the foregoing finding an Hp protein downregulates PMA-induced MCP-1 expression in HUVECs, an Hp protein can inhibit secretion of MCP-1 by inactivation of PKC.

Figure 2:
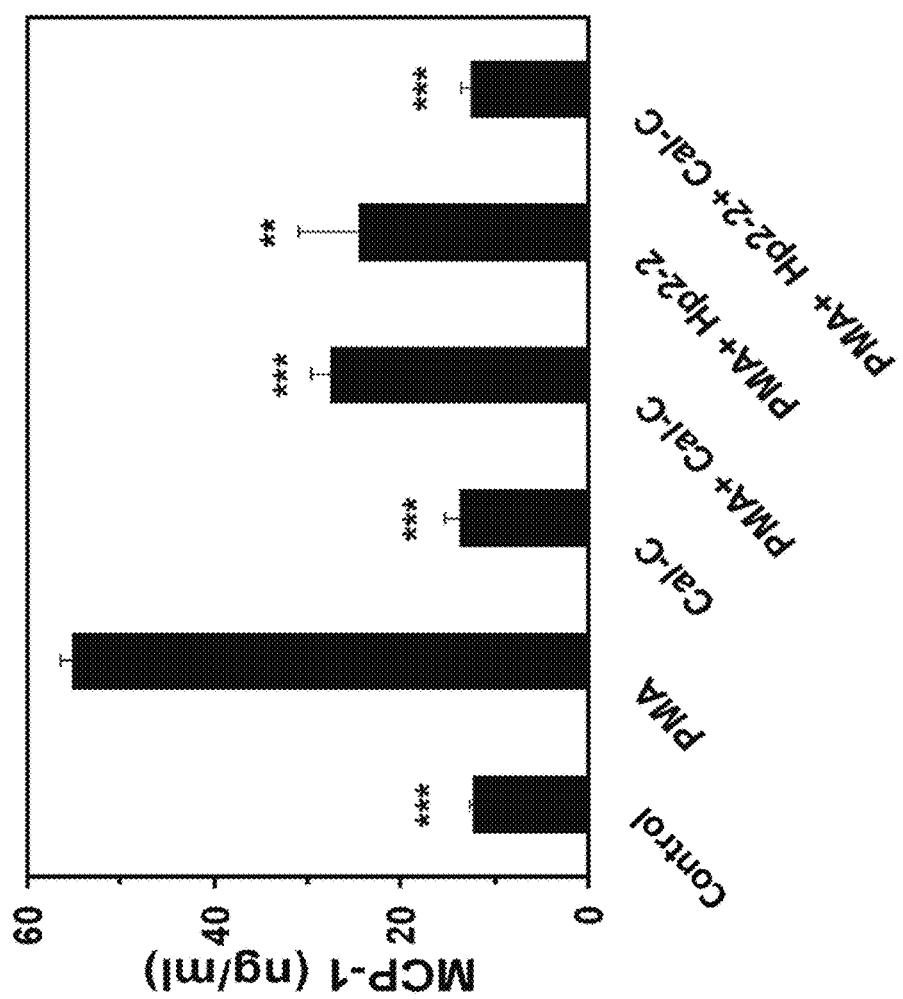
FIG. 2 is a bar graph illustrating MCP-1 protein expression level in Hp 2-2 protein-treated HUVECs.

As shown in FIG. 2, PKC and an Hp protein have effect on change of PMA-induced MCP-1 expression level in HUVECs. Specifically, these cells were pre-incubated with a PKC activator Calphostin C (Cal-C) in 5 μg/mL and/or 2 mg/mL of an Hp 2-2 protein for 8 hours, and then 100 ng/mL of PMA was added to these cells for other 8-hour incubation. Afterwards, each cell culture medium was analyzed by an enzyme-linked immunosorbent assay (ELISA). Compared with MCP-1 expression level of HUVECs merely treated with PMA, those of PMA and Cal-C-cotreated HUVECs, and PMA and Hp 2-2 protein-cotreated HUVECs are relatively low (FIG. 2).

Figure 3:
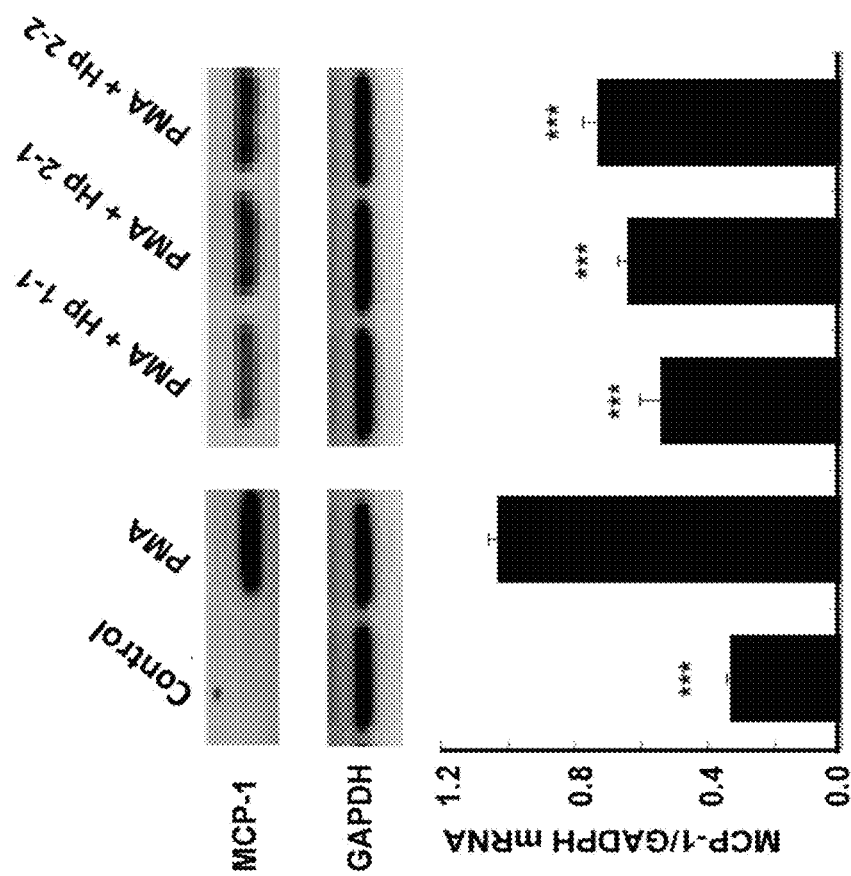
FIG. 3 is a reverse-transcription polymerase chain reaction analysis diagram illustrating MCP-1 mRNA expression level in HUVECs treated with various Hp phenotypes.

A reverse-transcription polymerase chain reaction (RT-PCR) analysis was used to quantify MCP-1 mRNA expression level in HUVECs under various conditions. Specifically, these cells were pre-cultured with 2 mg/mL of various Hp phenotypes for 8 hours, and then cultured with 100 ng/mL of PMA for 8 hours. After which, total RNA extracted from these cells was analyzed by RT-PCR. The result is shown in FIG. 3. MCP-1 mRNA expression level in PMA and Hp protein-cotreated HUVECs is lower than that in HUVECs merely treated with PMA.

EXAMPLE 3

Angiogenesis Test

Figure 4:
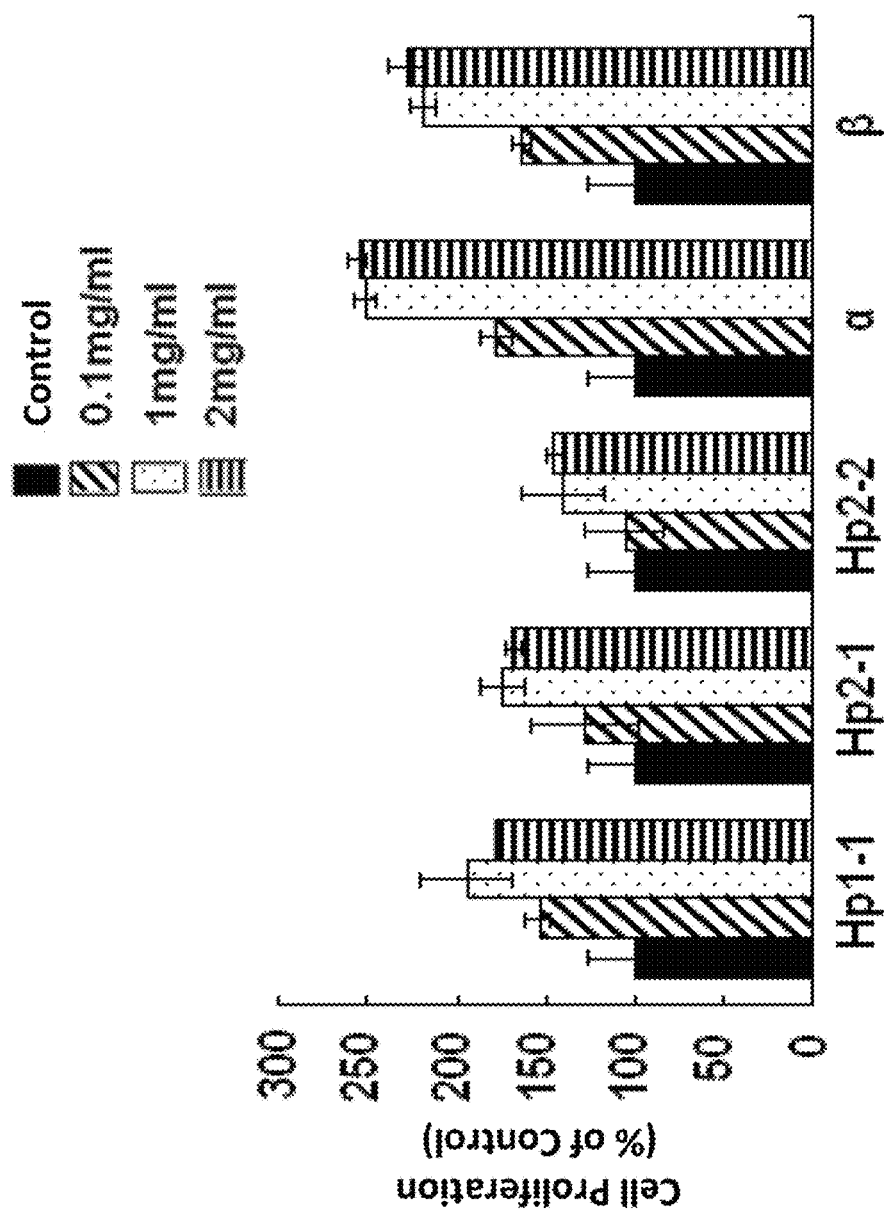
FIG. 4 is a bar graph illustrating effect of various Hp phenotypes and various Hp subunits on angiogenesis for HUVECs.

50 μL of growth factor reduced-Matrigel basement membrane matrix (Invitrogen) was placed onto a 24-well insert (Millipore) having a pore size of 0.45 μm. After the matrix was polymerized at 37° C. for 30 minutes, conditioned media containing 0.2 mg/mL of each Hp phenotype, an Hp α subunit, or an Hp β subunit was cultured with resuspended HUVECs seeded on the matrix in $1 \times 10^4$ cells/well for 16 hours. A microscope (Olympus BX51) was used to observe capillary formation by HUVECs, and three fields were randomly selected to measure the capillary length. The result is presented in FIG. 4. As compared with untreated HUVECs (control group), Hp-treated HUVEC, Hp α subunit-treated HUVECs, and Hp β subunit-treated HUVECs have greater ability in angiogenesis.

EXAMPLE 4

Cell Proliferation Test

Figure 5:
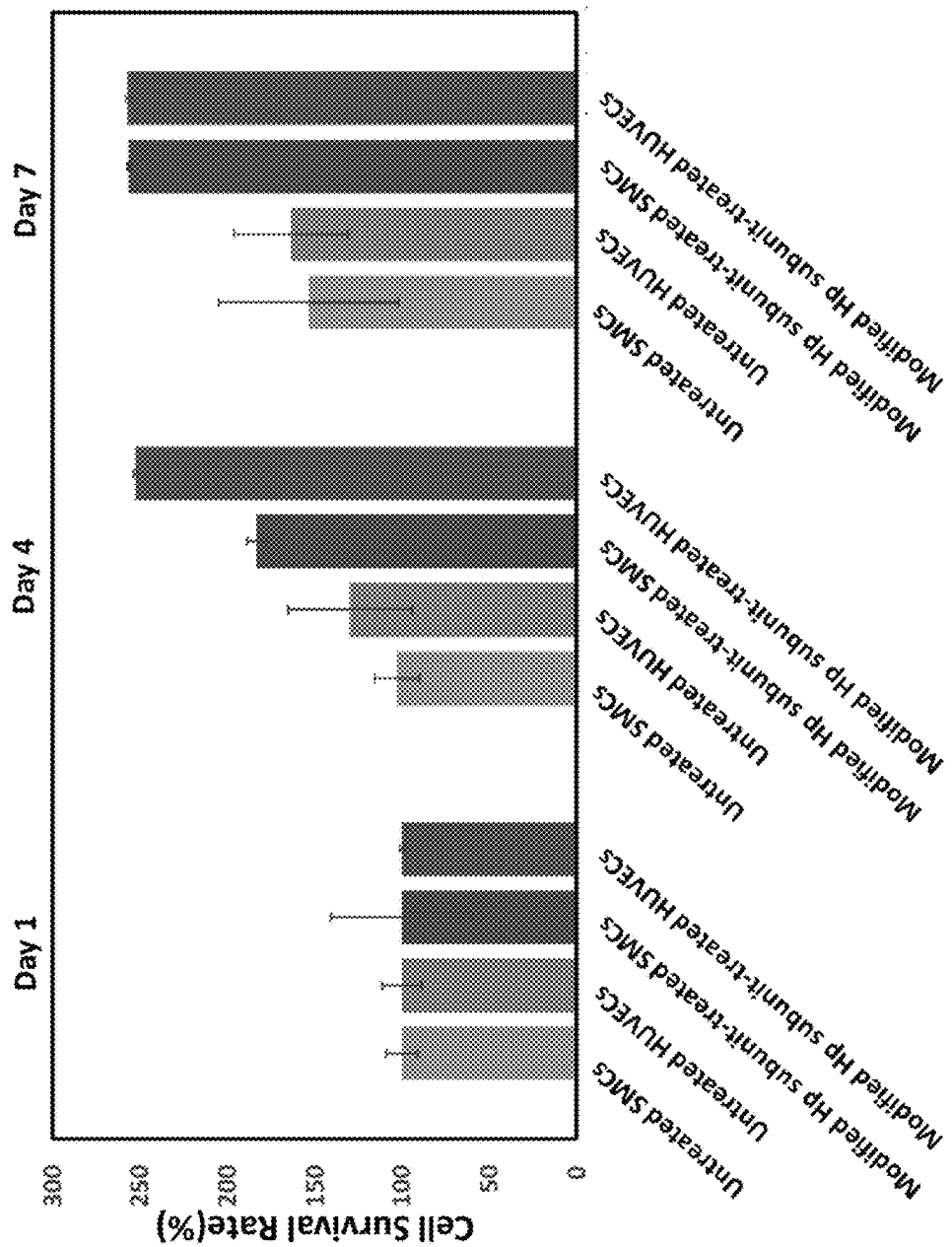
FIG. 5 is a bar graph illustrating survival rate of modified Hp subunit-treated SMCs and modified Hp subunit-treated HUVECs.

A 3-(4,5-dimethyl-thiazol-2-yl)-2,5-diphenyltetrazolium bromide (MTT) assay was used to analyze proliferation of smooth muscle cells (SMCs) and HUVECs. Firstly, SMCs were seeded into a 24-well plate in $1 \times 10^4$ cells/well; HUVECs were seeded into a 24-well transwell insert in $1 \times 10^4$ cells/well. At the 24th hour after seeding, these cells were cultured with EGM-2 medium containing a modified recombinant human Hp α or β subunit (one of SEQ ID NOs: 1-3) for 48 hours. An MTT reagent was added into each well in 480 μL/well, and reacted with these cells at 37° C. for 3 hours. Dimethyl sulfoxide (DMSO) was added to the product formazan, and incubated at dark for 30 minutes to dissolve the product. Finally, absorbance at 540 nm of the obtained solution was measured in a microplate reader. The measurement result is shown in FIG. 5. As compared with untreated SMCs, treated SMCs and treated HUVECs have a relatively high survival rate.

While the invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A method for promotion of angiogenesis, comprising: administering a modified haptoglobin subunit to a subject in need thereof, the modified haptoglobin subunit comprising an amino acid sequence selected from one of SEQ ID NOs: 1-3.

2. The method as claimed in claim 1, wherein the modified haptoglobin subunit is obtained via gene engineering or chemical synthesis.

3. The method as claimed in claim 1, wherein the modified haptoglobin subunit inhibits inflammatory response and/or promotes cell proliferation.

4. A method for treating a disease related to defective angiogenesis, comprising: administering a modified haptoglobin subunit to a subject in need thereof, the modified haptoglobin subunit comprising an amino acid sequence selected from one of SEQ ID NOs: 1-3.

5. The method as claimed in claim 4, wherein the modified haptoglobin subunit is obtained via gene engineering or chemical synthesis.

6. The method as claimed in claim 4, wherein the disease is selected from the group consisting of a cardiovascular disease, a myocardial infraction, and an ischemic disease.

7. The method as claimed in claim 4, wherein the modified haptoglobin subunit inhibits inflammatory response and/or promotes cell proliferation.

* * * * *

SEQUENCE LISTING

```
<160> NUMBER OF SEQ ID NOS: 3

<210> SEQ ID NO 1
<211> LENGTH: 82
<212> TYPE: PRT
<213> ORGANISM: Artificial Sequence
<220> FEATURE:
<223> OTHER INFORMATION: Synthesized

<400> SEQUENCE: 1

Val Asp Ser Gly Asn Asp Val Thr Asp Ile Ala Asp Asp Gly Ala Pro
1               5                   10                  15

Lys Pro Pro Glu Ile Ala His Gly Tyr Val Glu His Ser Val Arg Tyr
            20                  25                  30

Gln Cys Lys Asn Tyr Tyr Lys Leu Arg Thr Glu Gly Asp Gly Val Tyr
        35                  40                  45

Thr Leu Asn Asn Glu Lys Gln Trp Ile Asn Lys Ala Val Gly Asp Lys
    50                  55                  60

Leu Pro Glu Cys Glu Ala Val Ala Gly Lys Asp Lys Asn Pro Ala Asn
65                  70                  75                  80

Pro Val

<210> SEQ ID NO 2
<211> LENGTH: 141
<212> TYPE: PRT
<213> ORGANISM: Artificial Sequence
<220> FEATURE:
<223> OTHER INFORMATION: Synthesized

<400> SEQUENCE: 2

Val Asp Ser Gly Asn Asp Val Thr Asp Ile Ala Asp Asp Gly Ala Pro
1               5                   10                  15

Lys Pro Pro Glu Ile Ala His Gly Tyr Val Glu His Ser Val Arg Tyr
            20                  25                  30

Gln Cys Lys Asn Tyr Tyr Lys Leu Arg Thr Glu Gly Asp Gly Val Tyr
        35                  40                  45

Thr Leu Asn Asp Lys Lys Gln Trp Ile Asn Lys Ala Val Gly Asp Lys
    50                  55                  60

Leu Pro Glu Cys Glu Ala Asp Asp Gly Ala Pro Lys Pro Pro Glu Ile
65                  70                  75                  80

Ala His Gly Tyr Val Glu His Ser Val Arg Tyr Gln Cys Lys Asn Tyr
                85                  90                  95

Tyr Lys Leu Arg Thr Glu Gly Asp Gly Val Tyr Thr Leu Asn Asn Glu
            100                 105                 110

Lys Gln Trp Ile Asn Lys Ala Val Gly Asp Lys Leu Pro Glu Cys Glu
        115                 120                 125

Ala Val Ala Gly Lys Asp Lys Asn Pro Ala Asn Pro Val
    130                 135                 140

<210> SEQ ID NO 3
```

```
<211> LENGTH: 245
<212> TYPE: PRT
<213> ORGANISM: Artificial Sequence
<220> FEATURE:
<223> OTHER INFORMATION: Synthesized

<400> SEQUENCE: 3

Ile Leu Gly Gly His Leu Asp Ala Lys Gly Ser Phe Pro Trp Gln Ala
1               5                   10                  15

Lys Met Val Ser His His Asn Leu Thr Thr Gly Ala Thr Leu Ile Asn
            20                  25                  30

Glu Gln Trp Leu Leu Thr Thr Ala Lys Asn Leu Phe Leu Asn His Ser
        35                  40                  45

Glu Asn Ala Thr Ala Lys Asp Ile Ala Pro Thr Leu Thr Leu Tyr Val
50                  55                  60

Gly Lys Lys Gln Leu Val Glu Ile Glu Lys Val Val Leu His Pro Asn
65                  70                  75                  80

Tyr Ser Gln Val Asp Ile Gly Leu Ile Lys Leu Lys Gln Lys Val Ser
            85                  90                  95

Val Asn Glu Arg Val Met Pro Ile Ala Leu Pro Ser Lys Asp Tyr Ala
            100                 105                 110

Glu Val Gly Arg Val Gly Tyr Val Ser Gly Trp Gly Arg Asn Ala Asn
            115                 120                 125

Phe Lys Phe Thr Asp His Leu Lys Tyr Val Met Leu Pro Val Ala Asp
        130                 135                 140

Gln Asp Gln Cys Ile Arg His Tyr Glu Gly Ser Thr Val Pro Glu Lys
145                 150                 155                 160

Lys Thr Pro Lys Ser Pro Val Gly Val Gln Pro Ile Leu Asn Glu His
                165                 170                 175

Thr Phe Cys Ala Gly Met Ser Lys Tyr Gln Glu Asp Thr Cys Tyr Gly
            180                 185                 190

Asp Ala Gly Ser Ala Phe Ala Val His Asp Leu Glu Glu Asp Thr Trp
            195                 200                 205

Tyr Ala Thr Gly Ile Leu Ser Phe Asp Lys Ser Cys Ala Val Ala Glu
        210                 215                 220

Tyr Gly Val Tyr Val Lys Val Thr Ser Ile Gln Asp Trp Val Gln Lys
225                 230                 235                 240

Thr Ile Ala Glu Asn
                245
```